United States Patent [19]
Woodruff

[11] Patent Number: 5,420,681
[45] Date of Patent: May 30, 1995

[54] MODULAR MULTIPLE SPECTRAL IMAGER AND SPECTRAL IMAGER

[75] Inventor: Robert A. Woodruff, Boulder, Colo.

[73] Assignee: Ball Corporation, Muncie, Ind.

[21] Appl. No.: 101,419

[22] Filed: Aug. 3, 1993

[51] Int. Cl.$^6$ .............................. G01J 3/18; G01J 3/36
[52] U.S. Cl. ...................................... 356/326; 356/328
[58] Field of Search ............... 356/305, 326, 328, 334; 250/339.02

[56] References Cited

U.S. PATENT DOCUMENTS

| | | |
|---|---|---|
| 3,811,749 | 5/1974 | Abel . |
| 3,963,328 | 6/1976 | Abel . |
| 4,289,401 | 9/1981 | Mohr .................................. 356/305 |
| 4,411,499 | 10/1983 | Abel et al. . |
| 4,566,792 | 1/1986 | Suzuki ................................ 356/319 |
| 4,576,452 | 3/1986 | Abel et al. . |
| 4,773,756 | 9/1988 | Blechinger ......................... 356/334 |
| 4,820,048 | 4/1989 | Barnard .............................. 356/328 |
| 5,088,823 | 2/1992 | Smith, Jr. et al. ................. 356/328 |
| 5,139,335 | 8/1992 | Lundeen et al. ................... 356/328 |
| 5,260,767 | 11/1993 | Cook ............................... 356/328 X |

FOREIGN PATENT DOCUMENTS

2814058 1/1979 Germany .

OTHER PUBLICATIONS

Carruthers "Electrographic Instrumentation For Ultraviolet Imaging and Spectrography" SPIE vol. 172, Instrumentation in astronomy 20 Jan.-1 Feb. 1979, pp. 304-316.

NASA Brief "Integrated Grating Spectrometer" 1990 (Sep.) pp. 802.
"Hyperspectral Remote Sensing: Review of Current Capabilities," SETS, Inc. (May 1987).
"An efficient faint object spectrograph," C. G. Wynne, (Feb., 1982), Optica Acta, vol. 29 No. 2, 137–141.
"Stellar spectrograph with crossed dispersion," N. G. Zandin, O. N. Gusev and I. V. Peisakhson, (Jun. 1977). Sov. J. Opt. Technol 44(6) pp. 336–338.

*Primary Examiner*—Vincent P. McGraw
*Attorney, Agent, or Firm*—Gilbert E. Alberding

[57] ABSTRACT

A multiple spectral imager includes three modular imaging spectrometers, each having a respective collimator, dispersing element, and imaging system. Each collimator includes a pair of parabolic reflectors having a common focal point and an elongated slit positioned at the focal point, and each collimator defines a pupil near the respective dispersing element. The dispersing elements disperse light from various positions along the slit of the collimator into the respective imaging system, and each of the imaging systems includes an array detector that intercepts the dispersed light from the respective dispersing element and registers spectral information in a first direction and spatial information in a second direction. The spectrometers are stacked adjacent to one another, and light from a single directing mirror enters the collimators of all three of the spectrometers. The three array detectors are each responsive to a separate respective spectral region.

16 Claims, 5 Drawing Sheets

MODULAR MULTIPLE SPECTRAL IMAGER AND SPECTRAL IMAGER

BACKGROUND OF THE INVENTION

This invention, relates to a multiple spectral imager which utilizes a two-dimensional detector array to register spectral information in a first direction and spatial information in a second direction.

Multiple spectral imagers have been used in a variety of aircraft and spacecraft remote sensing imaging applications. Previously reported designs for such imagers include the designs known by the acronyms NIMS, VIMS, AVIRIS, SISEX, AIS and TIMS. These previous designs suffer from a variety of drawbacks, varying with the particular design. For example, several of these designs include a central obscuration, a relatively complex implementation or a difficult detector interface. In general, a central obscuration adds complexity to the configuration, reduces light collecting area, adds stray light, and adversely affects diffraction. The SISEX system utilizes a single collimator and a single spectrometer primary mirror to provide light to both short wave infrared (SWIR) and visible/near infrared (VNIR) spectrometers. This approach brings with it the need for a dichroic beam splitter to separate the SWIR and the VNIR optical paths.

The present invention is directed to a spectral imager which in the preferred embodiments described below eliminates the need for such dichroic beam splitters, and which takes a new approach to the optical layout for such an imager.

SUMMARY OF THE INVENTION

According to this invention, a multiple spectral imager is provided comprising two or more imaging spectrometers, each comprising a respective collimator, a respective dispersing element and a respective imaging system. Each of the collimators comprises a respective pair of parabolic reflectors having a common focal point and a respective elongated slit at the focal point, and each of the collimators defines a pupil near the respective dispersing element. Each of the dispersing elements disperses light from various positions along the slit of the respective collimator into the respective imaging system. Each of the imaging systems comprises a respective array detector that intercepts dispersed light from the respective dispersing element and registers spectral information in a first direction and spatial information in a second direction. The modular imaging spectrometers are stacked adjacent one another such that light from a single directing mirror enters the collimators of all of the imaging spectrometers, and the array detectors are each responsive to a separate respective spectral region.

The modular imaging spectrometers described below are compact, particularly in a direction along the length of the directing mirror. Because the multiple spectral imager is made up of modular imaging spectrometers, the construction of the imager is flexible, and individual spectrometers are readily replaced if necessary.

According to a second aspect of this invention, a spectral imager is provided, which can for example be used in the multiple spectral imager described above. This spectral imager comprises a collimator, a dispersing element and an imaging system. The collimator defines a pupil at the dispersing element, and the collimator comprises an elongated slit. The dispersing element disperses light from various positions among the slit of the collimator into the imaging system, and the imaging system comprises an array detector that intercepts the dispersed light from the dispersing element and registers spectral information in a first direction and spatial information in a second direction.

DETAILED DESCRIPTION OF THE PRESENTLY PREFERRED EMBODIMENTS

Figure 1:
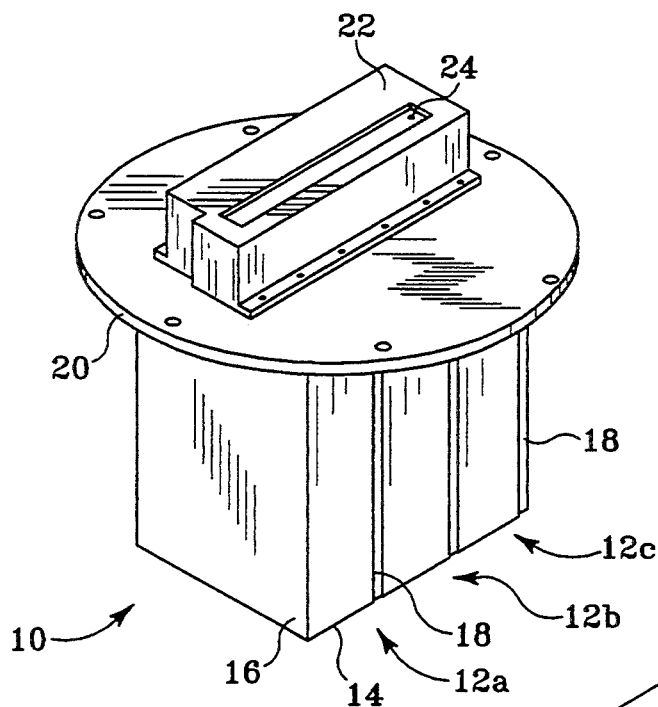
FIG. 1 is a top left perspective view of a multiple spectral imager which incorporates a presently preferred embodiment of this invention.
Figure 2:
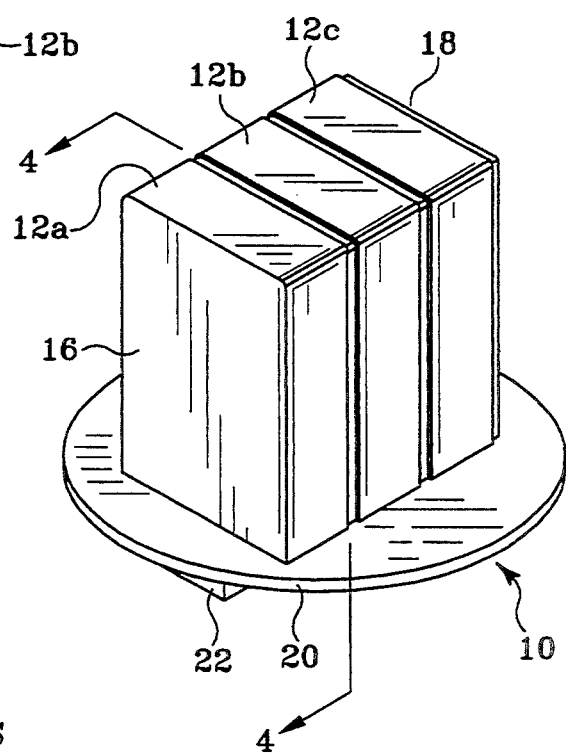
FIG. 2 is a bottom left perspective view of the multiple spectral imager of FIG. 1.
Figure 3:
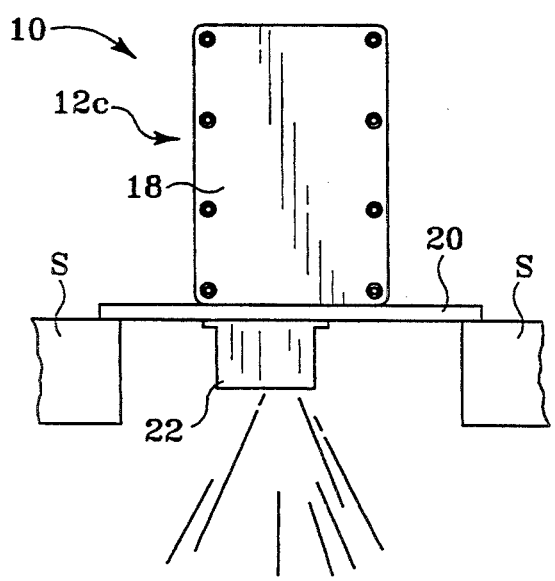
FIG. 3 is a right side elevational view of the multiple spectral imager of FIG. 1.

Turning now to the drawings, FIGS. 1 through 3 provide exterior views of a multiple spectral imager 10 that incorporates a presently preferred embodiment of this invention. The imager 10 achieves wide field multispectral imagery using unobscured optical systems. The imager is particularly compact for its optical capabilities, and the detector interface is made particularly simple by the use of refractive optics for the imaging systems. The multiple spectral imager 10 can be used for a wide range of aircraft and spacecraft remote sensing applications, in which the spectral signature is desired of all field positions contained within a large field of view, and in which a two-dimensional optical detector array is used for the measurement.

As best shown in FIGS. 1 and 2, the imager 10 includes three modular imaging spectrometers 12a, 12b, 12c. Each of these spectrometers includes a housing 14 which is made up of a rectangular body 16 and a cover 18. Each of the spectrometers 12a, 12b, 12c is a modular, self-contained unit, and all three of the spectrometers are rigidly secured to a mounting plate 20. The mounting plate 20 in turn supports a scan mirror housing 22 that defines a rectangular port 24. As shown in FIG. 1, this port 24 extends across all three of the spectrometers 12a, 12b, 12c.

Figure 4:
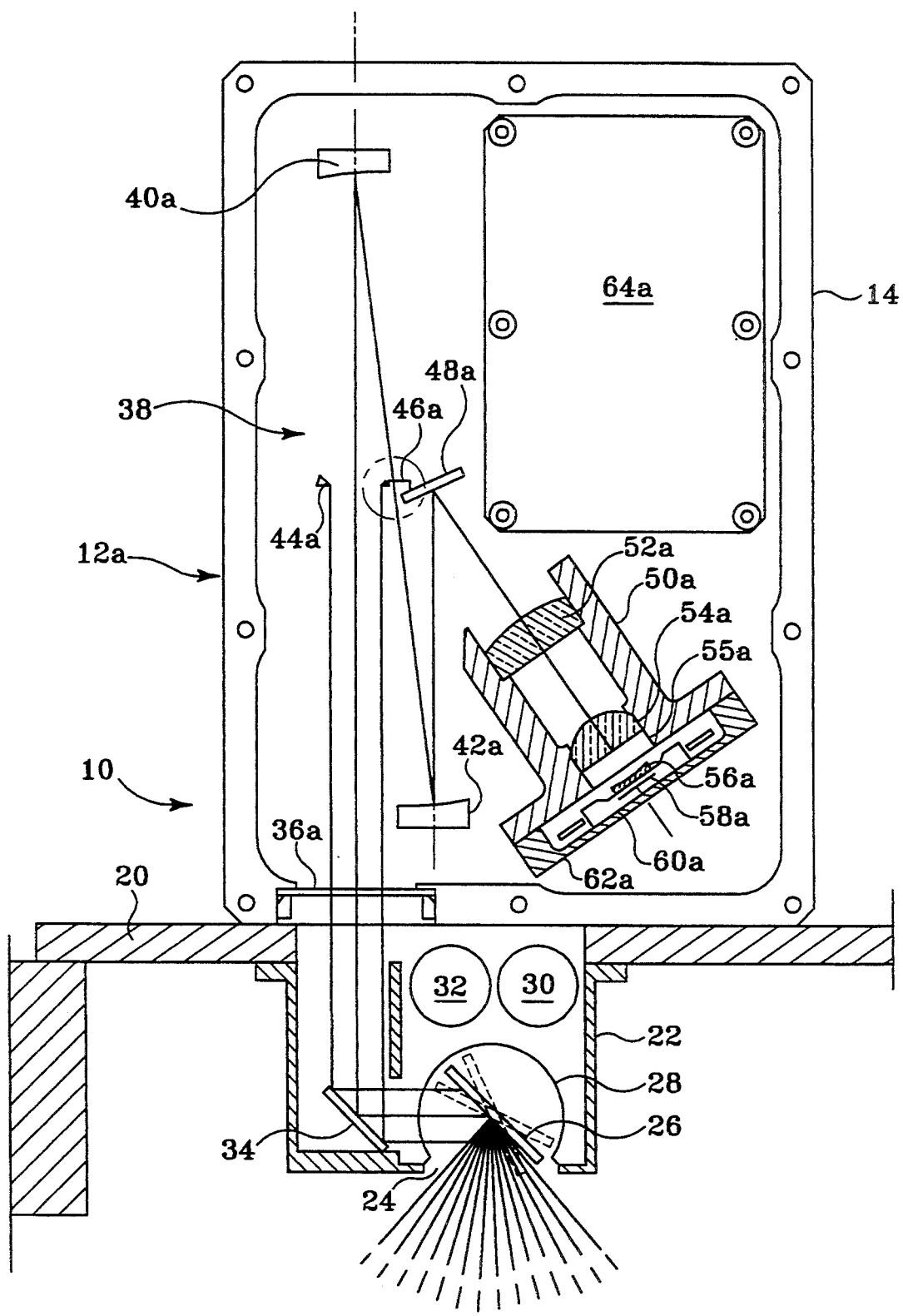
FIG. 4 is a cross sectional view taken along line 4—4 of FIG. 2.

FIG. 4 is a view of the internal components of the spectrometer 12a, and essentially corresponds to a view of the spectrometer 12a with the cover 16 of the housing 14 removed. As shown in FIG. 4, the scan mirror 26 is mounted for rotation by a scan mirror mount 28. The scan mirror 26 is scanned by a motor 30 through a 40 degree arc, as shown by the radiating rays, and the instantaneous position of the scan mirror 26 is measured by a shaft angle encoder 32. The scan mirror 26 directs light from the scene to a fold mirror 34, which directs the light through a window 36a into the modular imaging spectrometer 12a. The scan mirror 26 extends across all three of the spectrometers 12a, 12b, 12c, and the scan mirror 26 similarly directs light from the scene via the fold mirror 34 into the other imaging spectrometers 12b, 12c.

Still referring to FIG. 4, light from a distant scene, after reflecting from the plane scan and fold mirrors 26, 34, passes through the optical entrance pupil 44a and reflects from the telescope objective mirror 40a, an off-axis portion of a paraboloidal mirror of revolution which images the field at the field stop/spectrometer entrance slit 46a. The field of view is limited by coma from the telescope mirror, but a field of 10 degrees can be achieved.

In this embodiment the slit 46a is long and narrow. For example, the length of the entrance slit 46a can correspond to 10 degrees and the width is determined by the desired spatial and spectral resolution. Light passed by the slit 46a is reflected off of the spectrometer collimation mirror 42a, which is also an off-axis portion of a paraboloidal mirror of revolution. In this example the mirrors 40a, 42a have the same focal length, but this constraint is not required for all embodiments. The present invention could easily be implemented with non-matching focal lengths for the parabolic mirrors 40a, 42a. The collimation mirror 42a reflects incident light as a collimated beam directed to a dispersing element such as a grating 48a. The collimation mirror 42a reimages the entrance pupil 44a to form an optical pupil at the grating 48a. In this embodiment the grating 48a is a plane reflective diffraction grating. In alternative embodiments the dispersing element can be a transmissive diffraction grating or a prism placed at the optical pupil location.

The grating 48a disperses wave lengths from each field location along the length of the slit 46a, with dispersion being in the plane of FIG. 4.

The light dispersed by the grating 48a enters an imaging system 50a which in this embodiment includes a lens 52a, a doublet 54a, 55a, and a field flattening lens 56a. The imaging system 50a forms an image of the dispersed light at an image plane 58a. An array detector 60a is mounted with the active surface of the array detector at the image plane 58a. This array detector 60a is supported in place by an array detector support 62a. A printed circuit board assembly 64a is provided to process the signals generated by the array detector 60a and to control the position of the scan mirror 26.

The grating 48a is preferably placed near the reimaged pupil so that the entrance pupil of the imaging system 50a matches the pupil formed by the previous optics. When the grating 48a is positioned as described above, the field viewed by the imaging system 50a is symmetrical, with wavelength dispersion appearing as field in one direction and scene field of view appearing as field in the orthogonal direction. Analysis has indicated that the dispersing element can be positioned away from the pupil with some gradual loss in performance, and with the penalty of a larger dispersing element.

Figure 5:
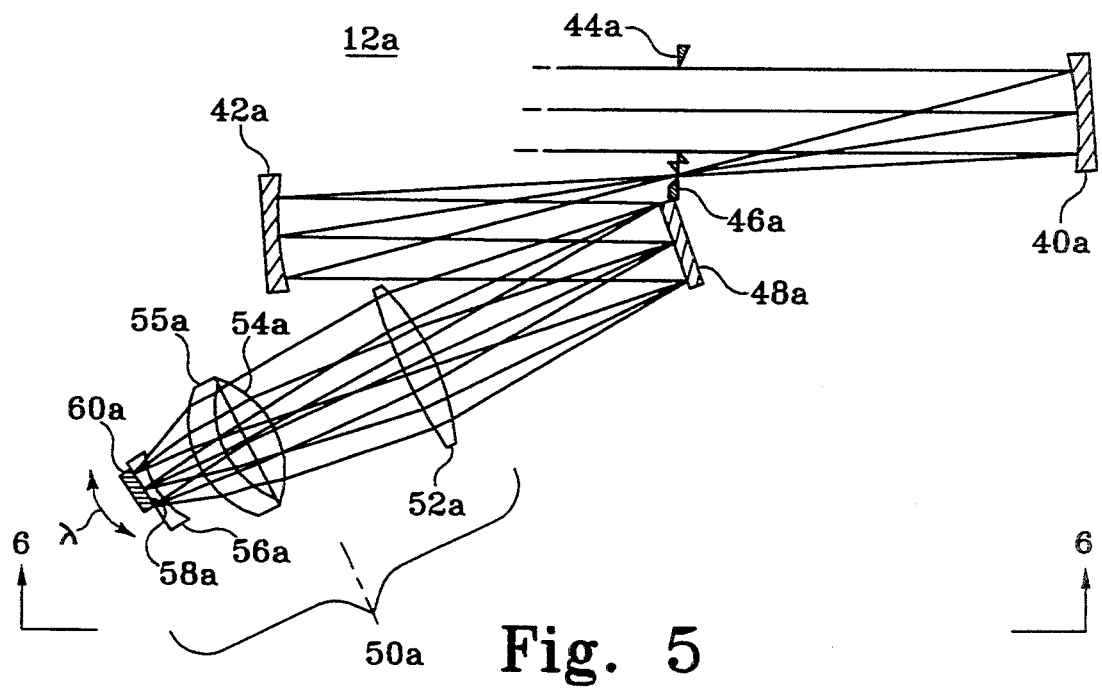
FIG. 5 is a side view showing the optical layout of the imaging spectrometer 12a of FIG. 1.
Figure 6:
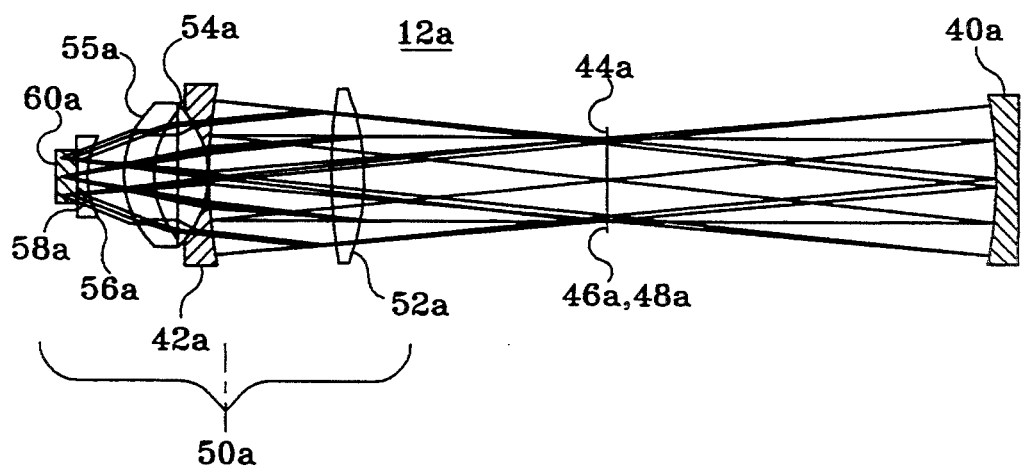
FIG. 6 is a top view showing the optical layout of the optical system of FIG. 5 taken along lines 6—6 of FIG. 5.
Figure 7:
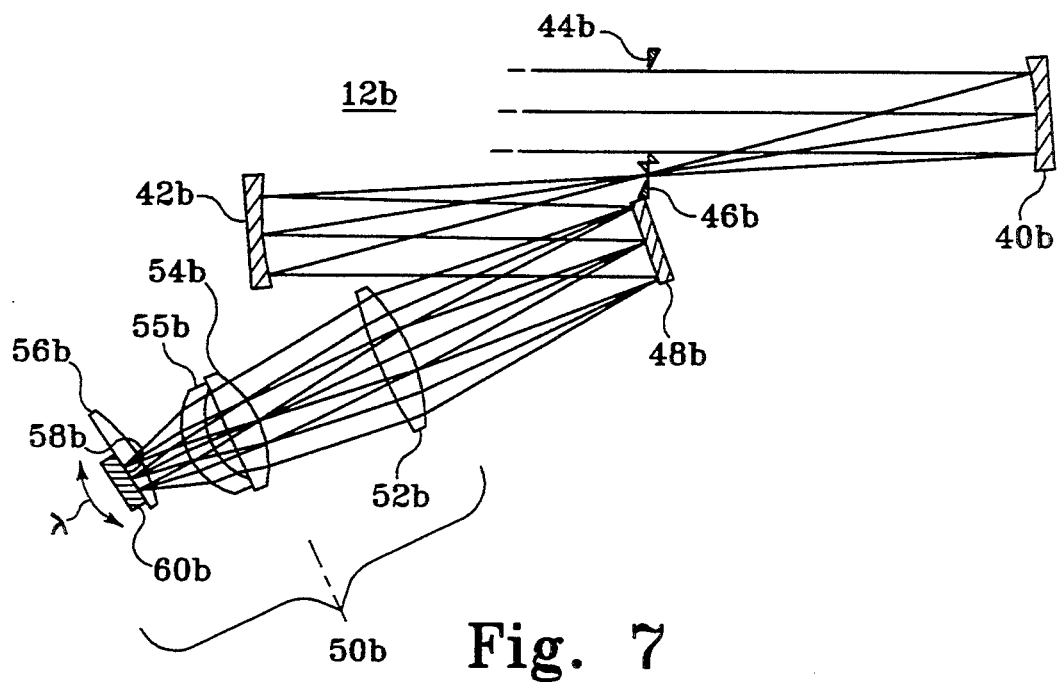
FIG. 7 is a side view showing the optical layout of the imaging spectrometer 12b of FIG. 1.
Figure 8:
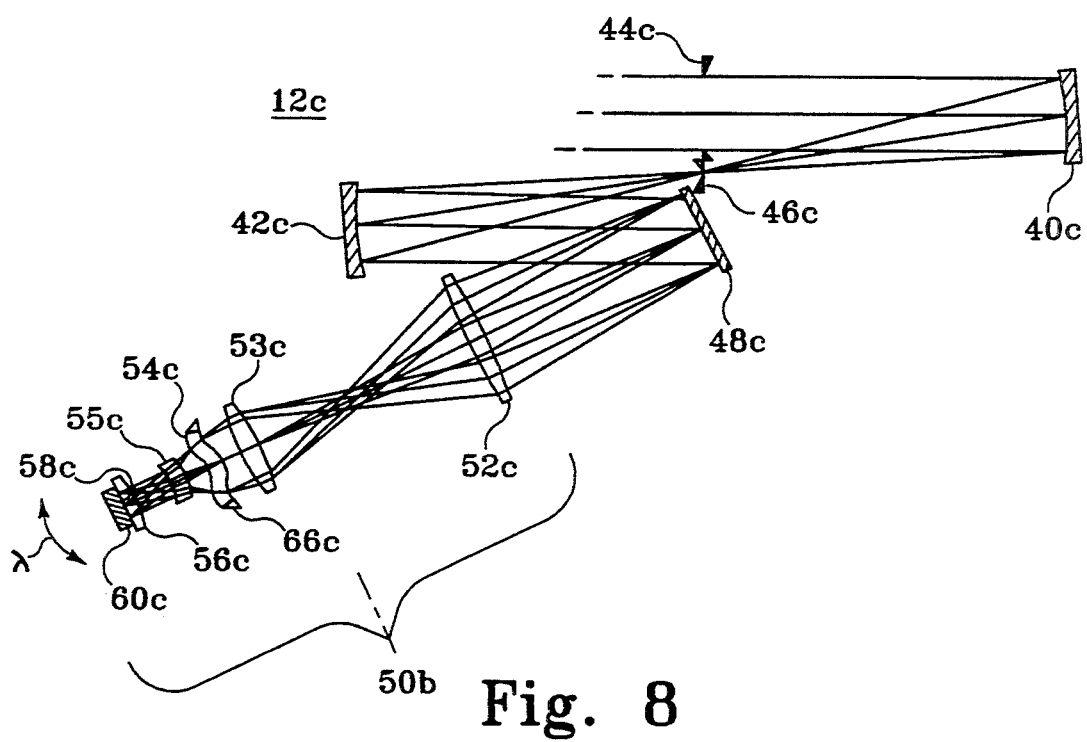
FIG. 8 is a side view showing the optical layout of the imaging spectrometer 12c of FIG. 1.

FIGS. 5 and 6 provide two views of the optical system of the imaging spectrometer 12a, and FIGS. 7 and 8 provide side views of the optical systems of the spectrometers 12b and 12c, respectively. FIGS. 7 and 8 use the same reference numerals as FIGS. 4-6 for comparable optical elements, with the appropriate letter suffix.

In this embodiment the imaging spectrometer 12a is a visible/near infrared (VNIR) spectrometer which fully covers the spectral region from 400 nm to 900 nm at a spectral resolution of 6 nm. The imaging spectrometer 12b of FIG. 7 in this embodiment is a short wave infrared (SWIR) spectrometer which fully covers the spectral region from 900 nm to 2500 nm at a spectral resolution of 13 nm. The imaging spectrometer 12c of FIG. 8 in this embodiment is a thermal long wave infrared (LWIR) spectrometer which fully covers the spectral region from 8,000 to 11,000 nm at a spectral resolution of 27 nm. Of course, the spectral and spatial coverage and the spectral resolving power and spatial resolution values can all be changed by design to meet the specific requirements of a given application.

In all three examples described above, the field coverage is 10 degrees (i.e., plus and minus 5 degrees). The design is fully symmetric in one axis about the center field location (i.e. symmetric about the plane of FIGS. 5, 7 and 8). The elongated slit 46a, 46b, 46c defines the field coverage and is oriented along a line transverse to the plane of FIGS. 5, 7 and 8, respectively. The direction of wavelength dispersion is in the plane of FIGS. 5, 7 and 8.

These designs use the two dimensions of the image plane 58a, 58b, 58c to sample each field position of the linear entrance slit over the full design spectral range. At the detector array, field position is displayed in one dimension, while the spectrum is displayed in the orthogonal direction. The single axis scan mirror 26 placed forward of the spectrometers 12a, 12b, 12c scans the entrance slits of the spectrometers across the scene so that a full two dimensional scene can be fully spectrally analyzed.

Figure 9:
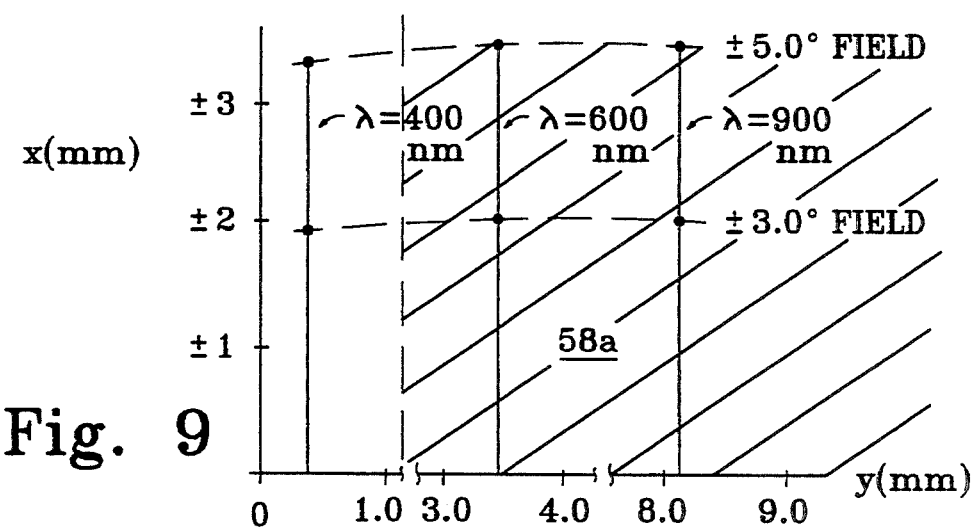
FIGS. 9, 10 and 11 are schematic representations of the image planes 58a, 58b, 58c of the imaging spectrometers 12a, 12b, 12c, respectively.
Figure 10:
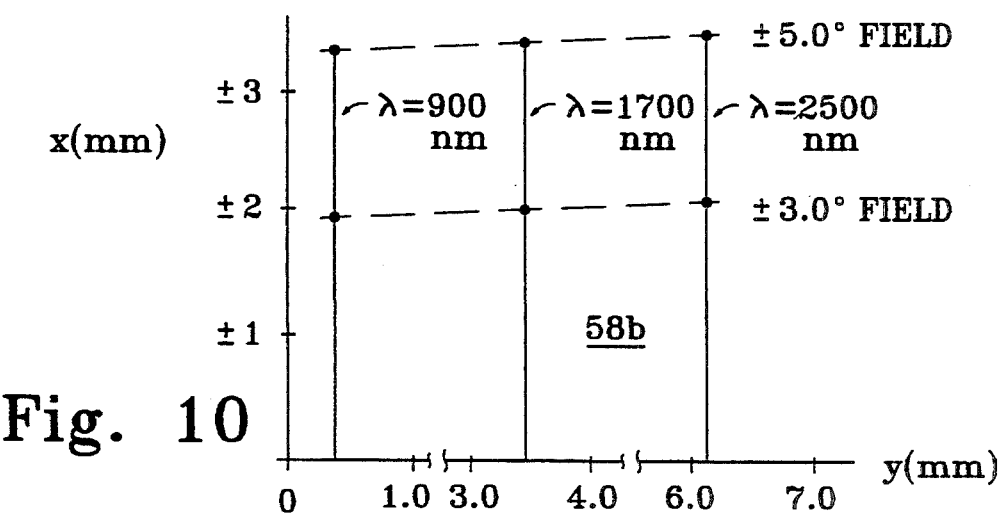
Figure 11:
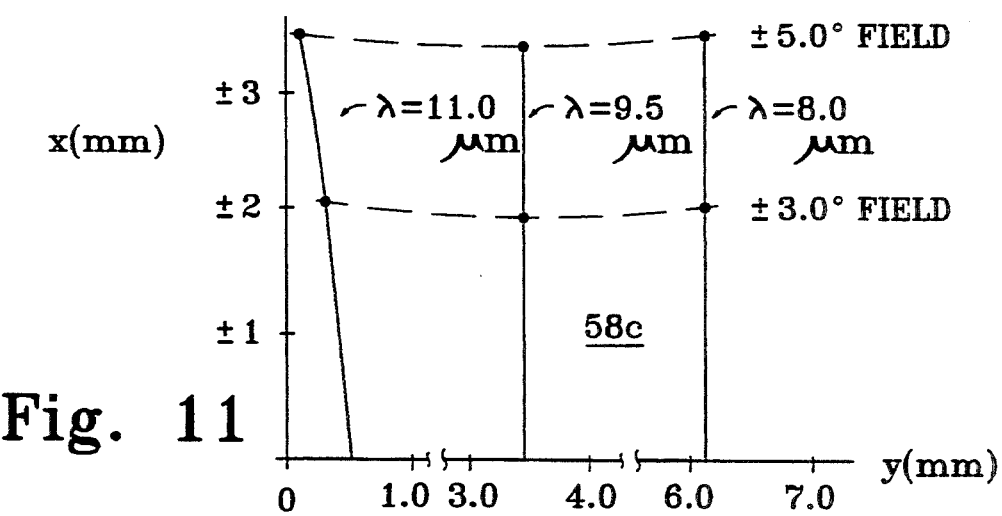

FIGS. 9, 10 and 11 provide schematic representations of the image planes 58a, 58b, 58c, respectively, for these three implementations. In these Figures the spatial axis and the spectral axis are shown at right angles to one another, and characteristic wavelengths are indicated as substantially vertical lines. While the formats of FIGS. 9, 10 and 11 are appropriate for a particular choice of aperture size, focal length, field of view, wavelength coverage, and other parameters, the present invention has broader application. The aperture size, focal length, lens materials, and other configuration parameters can all be modified to the requirements of a particular application.

Two different approaches for the imaging system optics are shown in FIGS. 5, 7 and 8. In both approaches the imaging system 50a, 50b, 50c images the scene field view onto the focal plane array along a direction transverse to the Figure and the scene spectrum along a direction parallel to the plane of the Figures. The approach shown in FIGS. 5 and 7 is well suited for VNIR and SWIR applications, and an exit pupil is not formed in front of the detector array. The approach shown in FIG. 8 provides an exit pupil 66c, an image of the intermediate pupil at the grating 48c, near the detector focal plane array. A cold pupil stop can be placed here to reduce background emitted by the instrument to the detector in thermal infrared (LWIR) implementations.

In all cases the final lens 56a, 56b, 56c is a field flattener. An order sorting filter can either be combined with the field flattener lens or can be provided as a separate filter. It has been discovered that a linear variable filter is useful here to further suppress background radiation onto the detector for infrared applications.

The focal plane array is placed directly behind the field flattener/order sorting filter 56a, 56b, 56c.

One of the novel aspects of the VNIR and SWIR embodiments lies in the order sorting filter. As noted above they each cover a wavelength range greater than a factor of two, and this embodiment uses the spectral range in first order. This would result in order sorting problems, but we place a longwave pass order sorting filter at the detector. The filter is spatially limited to cover only the region of the detector which would receive higher diffraction orders. For instance, the region of the array responding to 500-900 nm light, in the VNIR embodiment, is filtered with a longwave pass filter positioned immediately adjacent to the array detector to reject wavelengths less than 500 nm, as indicated schematically by the shaded region of FIG. 9. The rest of the array is unfiltered. This spatially varying order sorting filter effectively controls higher order diffracted light. The use of order sorting filters in this way reduces system mass, complexity, and cost by allowing us to fully cover the spectral region from 400 nm the 2500 nm with two spectrometers instead of three.

Simply by way of example, and without intending in any way to limit the scope of the following claims, the following Tables 1 through 6 define the presently preferred parameters for the imaging spectrometers 12a, 12b, 12c. The dimensions are stated in units of millimeters. As pointed out above, when the invention is adapted for other applications, many or all of these parameters can be varied.

TABLE 1

| Surface Number from Object to Image | Radius | Distance to Next Surface | Material | Notes |
|---|---|---|---|---|
| 0 | Plane | ∞ | Air | Object |
| 1 | −147.040 | −73.520 | Reflect | Mirror 40a, Parabolic |
| 2 | Plane | −73.520 | Air | Entrance Slit/ Field Stop |
| 3 | 147.040 | 73.520 | Reflect | Mirror 42a, Parabolic |
| 4 | Plane | −50.00 | Reflect | Grating 48a, Pupil |
| 5 | −45.885 | −6.00 | Fused Silica | Front surface of lens 52a |
| 6 | 131.349 | −25.860 | Air | Rear surface of lens 52a |
| 7 | −19.301 | −6.00 | Fused Silica | Front surface of lens 54a |
| 8 | 357.231 | −3.645 | Air | Rear surface of lens 54a |
| 9 | 22.441 | −5.00 | Fused Silica | Front surface of lens 55a |
| 10 | 22.300 | −10.00 | Air | Rear surface of lens 55a |
| 11 | 16.491 | −2.00 | Fused Silica | Front surface of lens 56a |
| 12 | Plane | −0.25 | Air | Rear surface of lens 56a |
| 13 | Plane | | | Image plane 58a |

TABLE 2

| Surface Number from Object to Image | Radius | Distance to Next Surface | Material | Notes |
|---|---|---|---|---|
| 0 | Plane | ∞ | Air | Object |
| 1 | −147.040 | −73.520 | Reflect | Mirror 40b, Parabolic |
| 2 | Plane | −73.520 | Air | Entrance Slit/ Field Stop |
| 3 | 147.040 | 73.520 | Reflect | Mirror 42b, Parabolic |
| 4 | Plane | −50.00 | Reflect | Grating 48b, Pupil |
| 5 | −33.233 | −6.00 | Fused Silica | Front surface of lens 52b |
| 6 | 310.046 | −25.663 | Air | Rear surface of lens 52b |
| 7 | −18.344 | −6.00 | Fused Silica | Front surface of lens 54b |
| 8 | 285.893 | −3.073 | Air | Rear surface of lens 54b |
| 9 | 15.825 | −5.00 | Fused Silica | Front surface of lens 55b |
| 10 | 16.286 | −10.00 | Air | Rear surface of lens 55b |
| 11 | −51.990 | −2.00 | Fused Silica | Front surface of lens 56b |
| 12 | Plane | −0.25 | Air | Rear surface of lens 56b |
| 13 | Plane | | | Image plane 58b |

TABLE 3

| Surface Number from Object to Image | Radius | Distance to Next Surface | Material | Notes |
|---|---|---|---|---|
| 0 | Plane | ∞ | Air | Object |
| 1 | −147.040 | −73.520 | Reflect | Mirror 40c, Parabolic |
| 2 | Plane | −73.520 | Air | Entrance Slit/ Field Stop |
| 3 | 147.040 | 73.520 | Reflect | Mirror 42c, Parabolic |
| 4 | Plane | −50.00 | Reflect | Grating 48c, Pupil |
| 5 | −150.00 | −3.00 | Germanium | Front surface of lens 52c, Hyperbolic, $K = -70.4$ |
| 6 | 150.00 | −50.00 | Air | Rear surface of lens 52c, Hyperbolic, $K = -35.1$ |
| 7 | −183.030 | −3.00 | Germanium | Front surface of lens 53c |
| 8 | 72.692 | −5.00 | Air | Rear surface of lens 53c |
| 9 | −10.779 | −3.00 | Germanium | Front surface of lens 54c |
| 10 | −10.640 | −5.00 | Air | Rear surface of lens 54c |
| 11 | −22.779 | −3.00 | Germanium | Front surface of lens 55c |
| 12 | −8.291 | −9.117 | Air | Rear surface of lens 55c |
| 13 | −58.541 | −2.00 | Germanium | Front surface of lens 56c |
| 14 | Plane | −0.25 | Air | Rear surface of lens 56c |
| 15 | Plane | | | Image plane 58c |

TABLE 4

| Grating | Line Spacing | Manufacturer and Part No. |
|---|---|---|
| 48a | 2.5 micron | Milton-Roy, 35-63-* - 581 |
| 48b | 10.0 micron | Milton-Roy, 35-53-* - 832 |
| 48c | 20.0 micron | Milton-Roy, 35-53-* - 850 |

TABLE 5

| Slit | Width | Length |
|------|-------|--------|
| 46a  | 0.10 mm | 13 mm |
| 46b  | 0.10 mm | 13 mm |
| 46c  | 0.10 mm | 13 mm |

TABLE 6

| Array Detector | Type | Geometry |
|----------------|------|----------|
| 60a | Si CCD | 512 × 512 Array, 18 micron pixels |
| 60b | InSb or HgCdTe | 128 × 128 Array, 50 micron pixels |
| 60c | HgCdTe | 128 × 128 Array, 50 micron pixels |

As used herein the term "light" is intended broadly to cover visible as well as ultraviolet and infrared electromagnetic radiation. It is not essential in all embodiments that the slit 46 be a transmitting slit, and if desired a reflector slit can be substituted. As pointed out above, the grating 48 can be replaced with a transmissive grating or a prism in alternative embodiments.

The multiple spectral imager described above has a fast f/number, in the range of f/2.4 to f/3.0. Such a fast f/number and the disclosed pupil locations allow a high signal to noise ratio and effective baffling. Central obscurations are avoided, thereby increasing the collection area, reducing stray light and reducing diffraction problems. The optical systems described above are relatively simple to implement, and they allow a detector to be interfaced in a simple manner. The entire design is compact and modular, and individual ones of the spectrometers 12a, 12b, 12c can be replaced in a convenient manner. All of these advantages are obtained in a imager that provides a wide field of view with good spatial resolution and wide spectral coverage with good resolving power.

Of course, it should be understood that a wide of changes and modifications can be made to the preferred embodiments described above. It is therefore intended that the foregoing detailed description be regarded as illustrative rather than limiting, and that it be understood that it is the following claims, including all equivalents, which are intended to define the scope of this invention.

I claim:

1. A multiple spectral imager comprising:
   first and second modular imaging spectrometers, each comprising a respective collimator, a respective dispersing element, and a respective imaging system;
   each of said collimators comprising a respective pair of parabolic reflectors having a common focal point and a respective elongated slit at the focal point, each of said collimators defining a pupil near the respective dispersing element;
   each of said dispersing elements dispersing light from various positions along the slit of the respective collimator into the respective imaging system;
   each of said imaging systems comprising a respective array detector that intercepts the dispersed light from the respective dispersing element and registers spectral information in a first direction and spatial information in a second direction; and
   a directing mirror;
   said first and second modular imaging spectrometers stacked adjacent one another such that light from the directing mirror enters the collimators of both of the imaging spectrometers;
   said array detectors each responsive to a separate respective spectral region.

2. The invention of claim 1 wherein at least one of the dispersing elements comprises a respective grating.

3. The invention of claim 1 wherein the first and second directions of each array detector are substantially orthogonal.

4. The invention of claim 1 wherein the parabolic reflectors in each pair define equal focal lengths.

5. The invention of claim 1 wherein each modular imaging spectrometer defines a maximum thickness measured parallel to the respective slit of less than 2 inches.

6. The invention of claim 1 wherein each of said imaging systems comprises a respective set of imaging lenses positioned and configured to image light from the respective dispersing element onto the respective detector array.

7. The invention of claim 1 wherein each of the imaging spectrometers further comprises a respective housing that encloses the respective collimator, dispersing element and imaging system.

8. The invention of claim 1 wherein each of the elongated slits passes transmitted light.

9. The invention of claim 2 wherein the imaging system comprising the grating comprises an order sorting filter positioned adjacent the respective array detector.

10. The invention of claim 9 wherein the order sorting filter varies spatially to filter only a portion of the respective array detector.

11. A spectral imager comprising:
    a collimator;
    a dispersing grating; and
    an imaging system;
    said collimator defining a pupil at the dispersing grating, and said collimator comprising an elongated slit;
    said dispersing grating dispersing light from various positions along the slit of the collimator into the imaging system;
    said imaging system comprising an array detector that intercepts the dispersed light from the dispersing grating and registers spectral information in a first direction and spatial information in a second direction; and
    an order sorting filter positioned adjacent the array detector, wherein the order sorting filter varies spatially to filter only a portion of the array detector.

12. The invention of claim 11 wherein the first and second directions are orthogonal.

13. The invention of claim 11 wherein said imaging system comprises a set of imaging lenses positioned and configured to image light from the dispersing element onto the detector array.

14. The invention of claim 11 wherein the collimator comprises a pair of parabolic reflectors having a common focal point, wherein the slit is positioned at the common focal point.

15. The invention of claim 11 wherein the parabolic reflectors define equal focal lengths.

16. The invention of claim 11 wherein the elongated slit passes transmitted light.

* * * * *